United States Patent [19]

Kinoshita et al.

[11] 4,451,548

[45] May 29, 1984

[54] ELECTROPHOTOGRAPHIC PHOTORECEPTOR

[75] Inventors: Akira Kinoshita; Osamu Sasaki; Kiyoshi Sawada; Satoshi Goto, all of Hino, Japan

[73] Assignee: Konishiroku Photo Industry Co., Ltd., Tokyo, Japan

[21] Appl. No.: 353,889

[22] Filed: Mar. 2, 1982

[30] Foreign Application Priority Data

Mar. 13, 1981 [JP] Japan .................. 56-36167

[51] Int. Cl.³ .................. G03G 5/06; G03G 5/14
[52] U.S. Cl. .................. 430/79; 430/76; 430/58; 548/136; 548/143; 548/440
[58] Field of Search .................. 430/76, 79, 58, 80; 542/454

[56] References Cited

U.S. PATENT DOCUMENTS

| 3,097,095 | 7/1963 | Klüpfel et al. | 430/76 |
| 3,112,197 | 11/1963 | Neugebauer et al. | 430/76 |
| 3,279,918 | 10/1966 | Cassiers et al. | 430/76 |
| 4,091,208 | 5/1978 | Okazaki et al. | 542/454 |
| 4,284,698 | 8/1981 | Kazami et al. | 430/76 |

FOREIGN PATENT DOCUMENTS

| 1108219 | 6/1961 | Fed. Rep. of Germany | 430/80 |
| 1129947 | 5/1962 | Fed. Rep. of Germany | 430/79 |
| 51-94828 | 8/1976 | Japan | 430/76 |
| 55-36138 | 9/1980 | Japan | 430/79 |

*Primary Examiner*—Edward C. Kimlin
*Assistant Examiner*—Merrell C. Cashion
*Attorney, Agent, or Firm*—Frishauf, Holtz, Goodman & Woodward

[57] ABSTRACT

Disclosed is an electrophotographic photoreceptor which comprises, on an electroconductive support, a light sensitive layer containing a carrier generation material, a carrier transport material consisting of a carbazole derivative represented by the following general formula I:

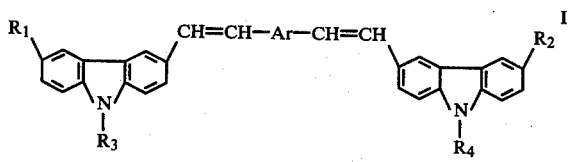

where $R_1$, $R_2$, $R_3$, $R_4$ and Ar are as defined in the specification.

11 Claims, 7 Drawing Figures

ELECTROPHOTOGRAPHIC PHOTORECEPTOR

BACKGROUND OF THE INVENTION

The present invention relates to an electrophotographic photoreceptor comprising an organic photoconductive compound as the principal component.

More particularly, the present invention is concerned with an electrophotographic photoreceptor which is highly sensitive and durable and comprises a light sensitive layer on a conductive support, said layer containing a carrier generation material and a carrier transport material.

Heretofore, as an electrophotographic photoreceptor, there has been well known the one comprising an inorganic photoconductive material such as selenium, zinc oxide or cadmium sulfide as the principal component. However, such a photoreceptor has not been necessarily satisfactory since, for instance, in the case of a selenium photoreceptor, the thermal stability has been inadequate, in the case of a zinc oxide photoreceptor, the durability has been poor, and in the case of a cadmium sulfide photoreceptor, there have been problems with respect to the toxicity and weak moisture resistance.

On the other hand, an electrophotographic photoreceptor comprising an organic photoconductive compound as the principal component is generally superior in its thermal stability and has various advantages such that, in addition to the fact that it is free of toxicity like a heavy metal salt, it is relatively easy to manufacture, is inexpensive and easy to handle.

For these advantages, attention has been drawn in recent years to the electrophotographic photoreceptor using an organic photoconductive compound, and various proposals have been made.

For instance, there have been proposals in the specification of U.S. Pat. No. 3,037,861 where poly-N-vinylcarbazol is used as the photoconductive material, in the specification of U.S. Pat. No. 3,180,729 where pyrazoline is used as the photoconductive material, in the specification of U.S. Pat. No. 3,180,730 where a triaryl amine is used as the photoconductive material, in the specification of U.S. Pat. No. 3,189,447 where oxadiazole is used as the photoconductive material, and in Japanese Patent Publication No. 10983/1976 where a diaryl alkane is used as the photoconductive material. However, these have been inferior to photoreceptors comprising inorganic photoconductors as the principal components, in their important electric characteristics for electrophotographic photoreceptors, such as sensitivity and residual electric potential.

However, there has been a proposal for a function-separating type photoreceptor in which the carrier generation function and the carrier transport function are assigned to separate substances, respectively, for instance, a photoreceptor having a light sensitive layer having a double phase structure containing the carrier transport material and the carrier generation material in a mixed state as a dispersion or a solid solution, or a photoreceptor having a light sensitive layer of a double layer structure prepared by laminating a carrier generation layer containing the carrier generation material and a carrier transport layer containing the carrier transport material. With such a function-separating type photoreceptor, the range of the materials that may be used for the preparation of the light sensitive layer is widened, and it is possible to independently select the substances or the substance systems to provide the respective optimal functions, whereby it becomes possible to prepare a light sensitive layer having superior characteristics required for the electrophotographic process, such as an electric charge retention power, sensitivity, stability in repeated uses, or film strength.

There have been some inventions proposed for various combinations of the carrier generation substances and the carrier transport material in such function-separating type photoreceptors. For instance, there are those disclosed in Japanese Patent Publication No. 16198/1968, the specification of U.S. Pat. No. 3,573,906, the specification of U.S. Pat. No. 3,837,851, the specification of U.S. Pat. No. 3,871,882 and Japanese Laid-Open Patent Application No. 84943/1980.

These electrophotographic photoreceptors have good initial electric characteristics. However, when used repeatedly, they bring about a decrease in the quantity of electric charge or an increase of the residual electric potential, and accordingly, if they are used repeatedly, the decrease in the image density or the increase in fogging becomes distinctive. Thus, under the factual situation, none of them are totally satisfactory as the electrophotographic photoreceptors.

An object of the present invention is to eliminate these drawbacks and to provide an electrophotographic photoreceptor which is superior in the electric charge acceptance and has a high sensitivity and low residual electric potential.

Another object of the present invention is to provide an electrophotographic photoreceptor which undergoes minimal changes in various characteristics such as the electric charge acceptance, sensitivity or residual electric potential, even when used repeatedly or even when subjected to heat or light, i.e. which undergoes minimal fatigue degradations of the electric characteristics.

A further object of the present invention is to provide an electrophotographic photoreceptor which has a great film strength and good physical durability.

A still further object of the present invention is to provide a novel carrier transport material which has a superior carrier transport material in a function-separating type photoreceptor containing a carrier generation material and a carrier transport material.

DESCRIPTION OF THE INVENTION

The above objects can be accomplished by a function-separating type electrophotographic photoreceptor comprising a carrier generation material and a carrier transport material, in which a carbazole derivative represented by the following general formula I is incorporated in the light-sensitive layer:

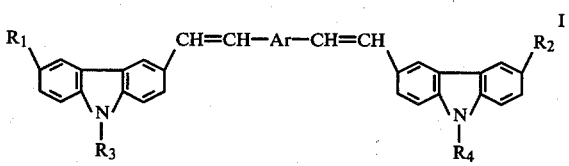

where each of $R_1$ and $R_2$ represents a hydrogen atom, a halogen atom, a hydroxyl group, a substituted or unsubstituted alkyl group, an alkoxy group, an aryloxy group, a substituted amino group, or a substituted or unsubstituted aryl group, each of $R_3$ and $R_4$ represents a substituted or unsubstituted aryl group, and Ar represents a substituted or unsubstituted arylene group or a heterocyclic aromatic group containing oxygen or sulfur.

The above-mentioned heterocyclic group is preferably a five- or six-membered ring comprising a nitrogen, an oxygen or a sulfur atom in addition to carbon atoms.

A preferred arylene group is a phenylene group or a naphthylene group, and a preferred heterocyclic aromatic group is a thiophen-di-yl group, a thiadiazol-di-yl group, or an oxadiazol-di-yl group.

In the present invention, as an atom or a group capable of substituting each group mentioned above, anyone can be recited. However, the preferred atoms or groups include a halogen atom, a hydroxyl group, an alkyl group, an aryl group, a heterocyclic group, an alkoxy group and a substituted amino group, and the groups just recited may further be substituted by an atom or a group.

As the carbazole derivative represented by the above general formula I and which is useful in the present invention, there may be mentioned, for instance, those having the following formulas:

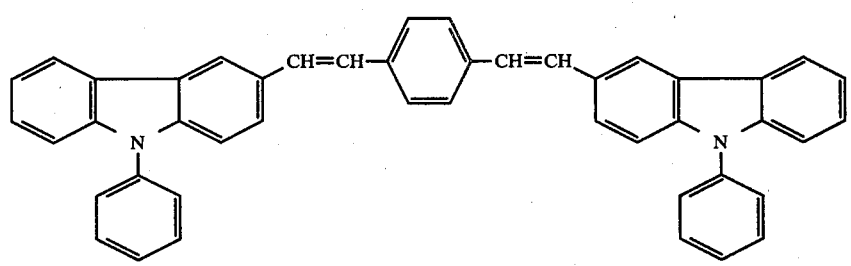

(1)

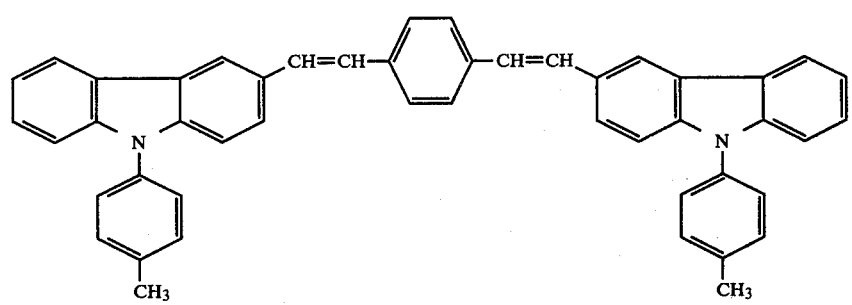

(2)

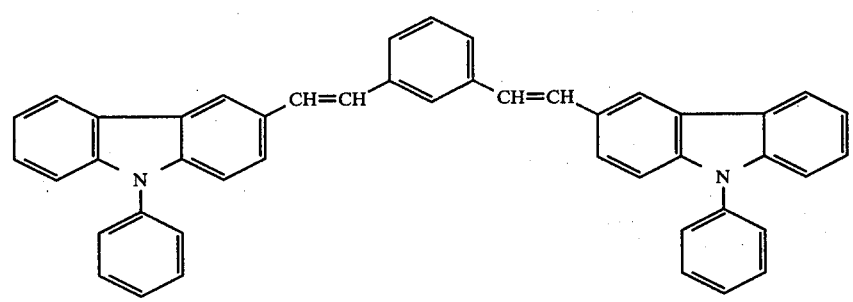

(3)

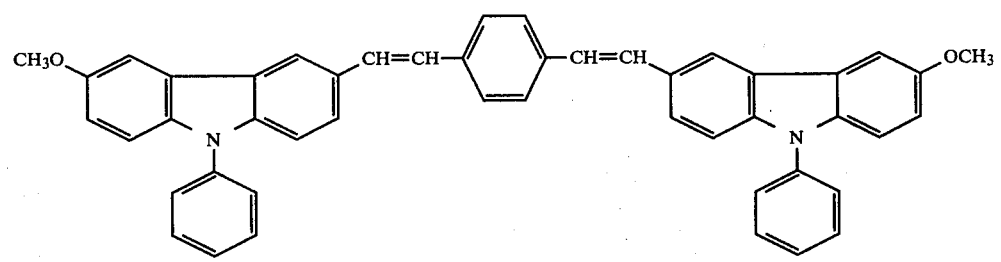

(4)

-continued
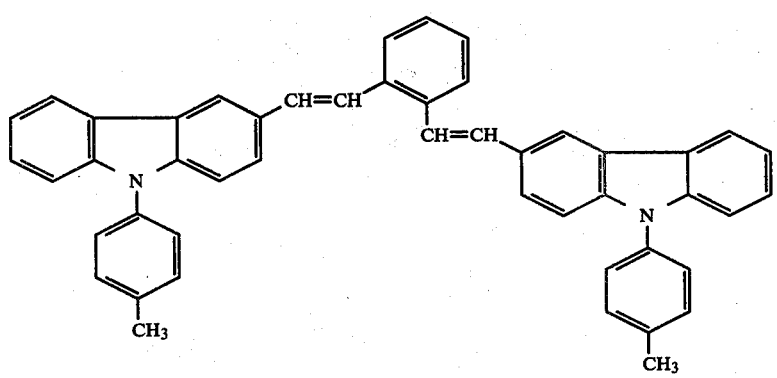
(5)
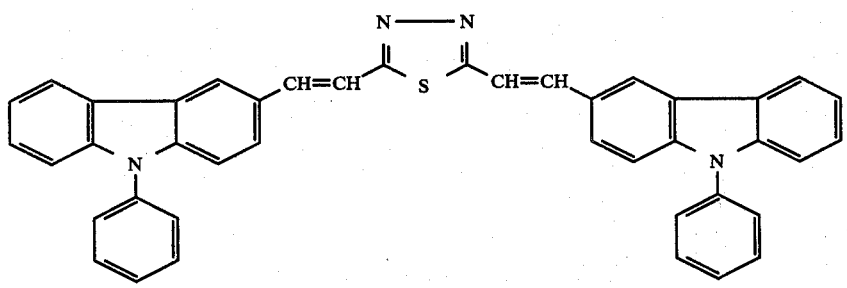
(6)
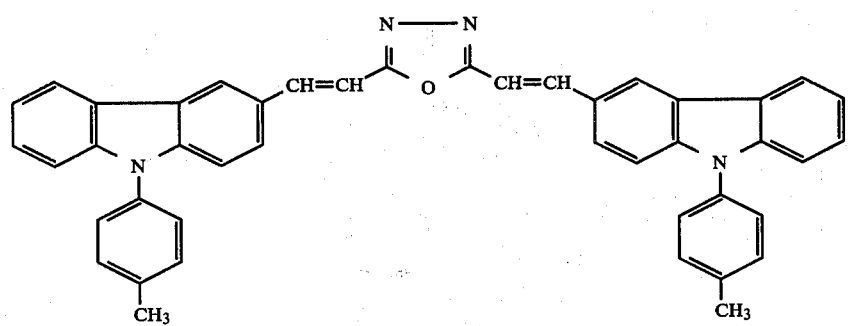
(7)
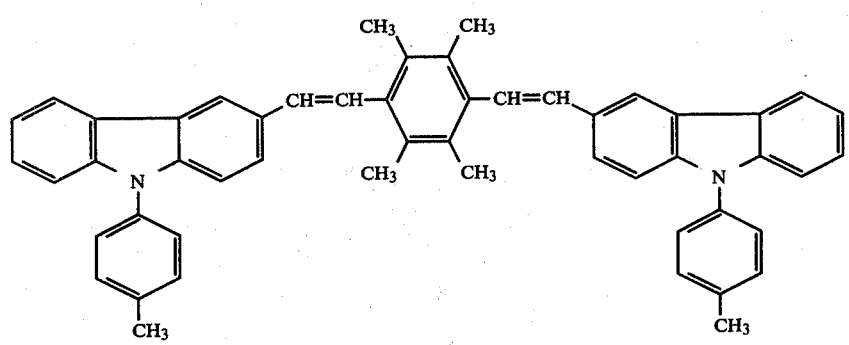
(8)

-continued
(9)
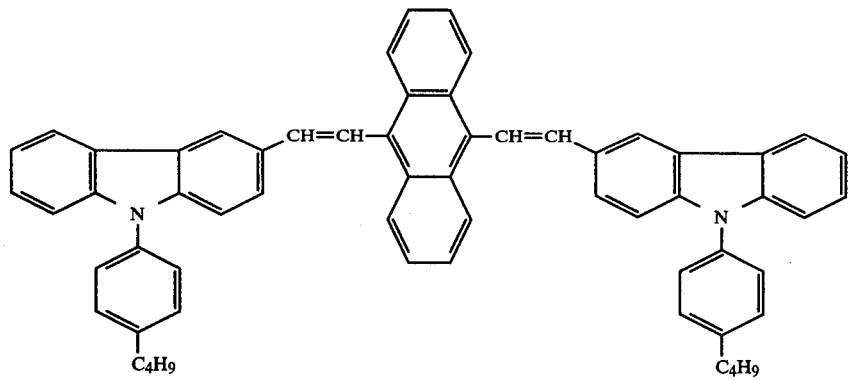
(10)
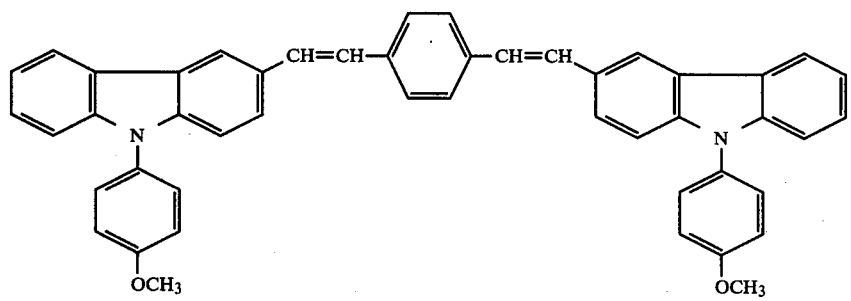
(11)
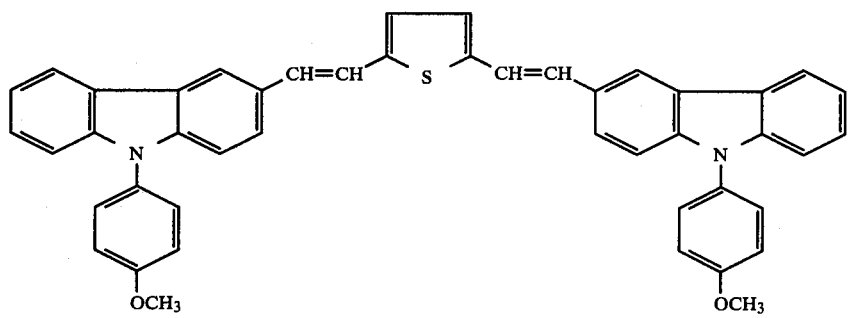
(12)
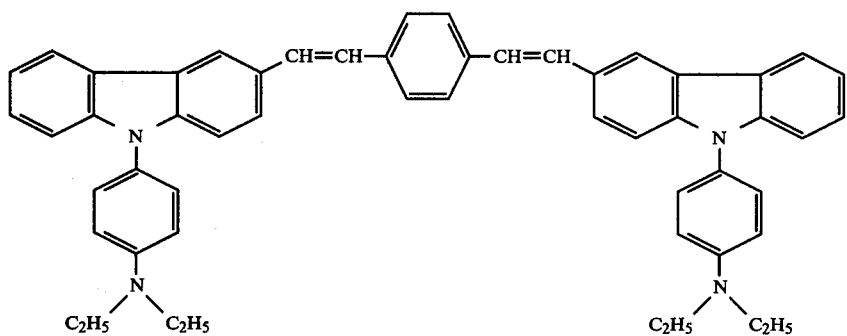
(13)
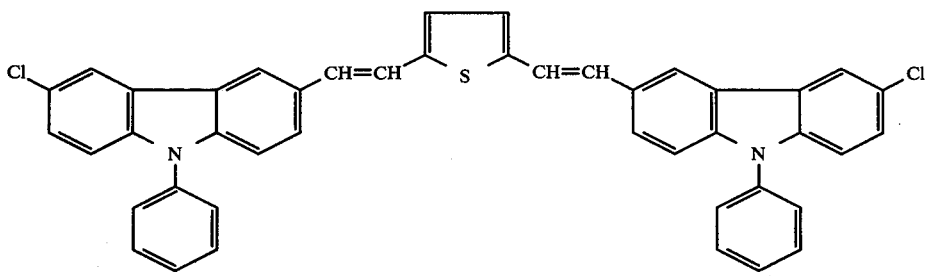

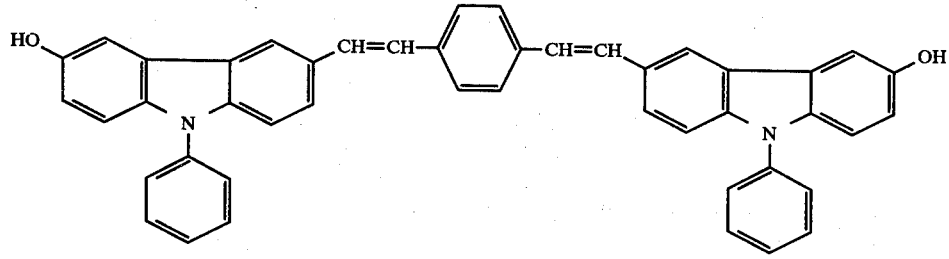

(14)

The carbazole derivatives of the present invention may readily be synthesized by a known method, for instance, the method disclosed in the specification of German Pat. No. 1,108,219 or the specification of German Pat. No. 1,129,947.

Namely, they may be synthesized by condensing a proper diester of phosphonic acid and a proper carbazole-3-carbaldehyde in N,N-dimethylformamide in the presence of a strong base.

Now, examples for the preparation of the carbazole derivatives according to the present invention will be described specifically in reference to the accompanying drawings, in which.

SYNTHESIS EXAMPLE 1

(Synthesis of the illustrated compound (1))

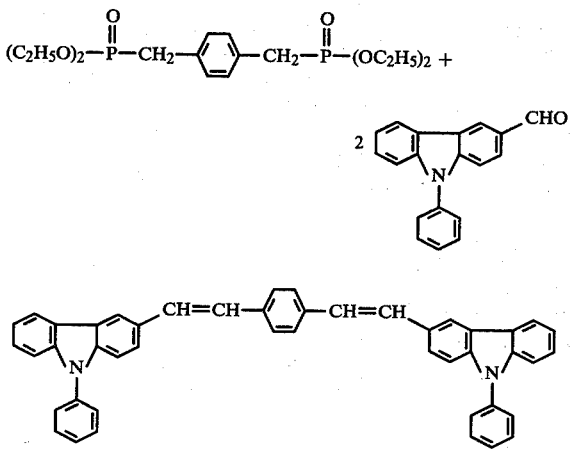

Figure 1:
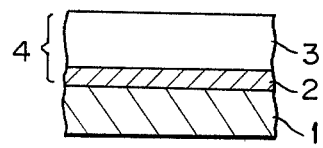
FIGS. 1 to 6 are cross-sectional views which show, respectively, embodiments of the physical structures of the electrophotographic photoreceptors according to the present invention.

To 20 ml of N,N-dimethylformamide, 1.36 g (20 m mol) of sodium ethoxide and 1.89 g (5 m mol) of tetraethyl α,α'-xylylene diphosphonate were added, and while stirring the mixture under cooling, 20 ml of a N,N-dimethylformaldehyde solution containing 2.71 g (10 m mol) of N-phenylcarbazole-3-carbaldehyde was dropwise added. After stirring the mixture at room temperature for 3 hours, it was further stirred at 80° C. for one hour. The reaction product was poured into 20 ml of ice water, and the precipitated crystals were filtered and recrystallized from N,N-dimethylformamide, whereupon the illustrated compound was obtained. The yield was 2.1 g (70.0%) and the melting point was 292° to 297° C.

SYNTHESIS EXAMPLE 2

(Synthesis of the illustrated compound (3))

To 20 ml of N,N-dimethylformamide, 1.36 g of sodium ethoxide and 1.89 g of tetraethyl α,α'-xylylene diphosphonate were added. While cooling the mixture, 20 ml of a hot N,N-dimethylformamide solution containing 2.85 g (10 m mol) of N-tolylcarbazole-3-carbaldehyde was dropwise added, and the mixture was stirred at room temperature for 3 hours and further stirred at 80° C. for 5 hours. The reaction mixture was poured into 20 ml of ice water, and the precipitated crystals were filtered and recrystallized from N,N-dimethylformamide, whereupon the illustrated compound (3) was obtained. The yield was 3.0 g (93.8%) and the melting point was 240° to 245° C.

The above mentioned carbazole derivatives may be used alone and as a mixture of two or more, or may be used in combination with an optional one selected from other carrier transport substances.

The carbazole derivatives of the present invention do not per se have a film forming capability, and accordingly, it is combined with various binders to form a light sensitive layer. Here, any optional binder may be used. However, hydrophobic electroinsulating polymers have a high dielectric constant are preferred. As such polymers, there may be mentioned, for instance, a polycarbonate, a polyester, a methacrylic resin, an acrylic resin, a polyvinyl chloride, a polyvinylidene chloride, a polystyrene, a polyvinyl acetate, a styrene-butadiene co-polymer, a vinylidene chloride-acrylonitrile copolymer, a vinyl chloride-vinyl acetate copolymer, a vinyl chloride-vinyl acetate-anhydrous maleic acid copolymer, a silicone resin, a silicone-alkyd resin, a styrene-alkyd resin, and a phenol-formaldehyde resin. These binders may be used alone or as a mixture of two or more.

Into a layer containing the carrier transport material as described above, an optional one selected from various carrier generation material which are capable of generating a carrier upon absorption of light, may be incorporated whereby a light sensitive layer of the function-separating type photoreceptor can effectively be formed.

As the carrier generation material which may be used for the photoreceptors of the present invention, there may be mentioned, for instance, the following: inorganic photoconductors such as selenium, selenium alloys, CdS, CdSe, CdSSe, or HgS; perylene dyestuffs such as perylene tetracarboxylic anhydride or perylene tetracarboxylic diimide; indigoid dyestuffs; polycyclic quinones such as anthraquinones, flavanthrones, or anthanthrones; bisbenzimidazole dyesftuffs; quinachridone dyestuffs; azo dyestuffs such as monoazo dyestuffs, bisazo dyestuffs or trisazo dyestuffs; indanthrone dyestuffs; squarylium dyestuffs; phthalocyanine dyestuffs; charge-transfer complexes composed of electron donating substances such as poly-N-vinylcarbazole and electron acceptor substances such as trinitrofluorenone; or co-crystalline complexes composed of a pyrylium salt or a thiapyrylium salt and polycarbonate. These carrier generation materials may be used alone or in combination of two or more. Further, in a case where a substance having per se no film forming capability is to be formed into a layer, an optional binder may be selected from the same binders as used for the carrier transport layer.

Figure 2:
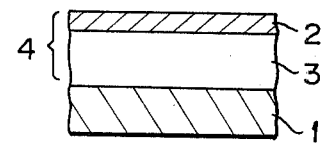
Figure 3:
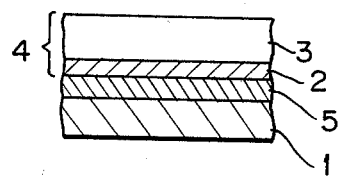
Figure 4:
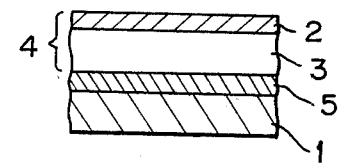
Figure 5:
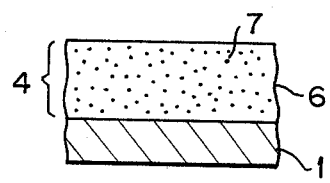
Figure 6:
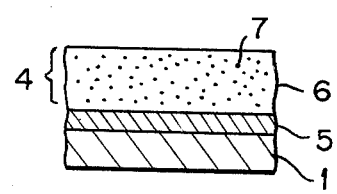

The physical structures of the electrophotographic photoreceptor of the present invention are as shown in FIGS. 1 and 2, in which a light sensitive layer 4 comprising a carrier forming layer 2 composed mainly of a carrier generation material and a carrier transport material composed mainly of a carrier transport material, is provided on an electroconductive support 1. As shown in FIGS. 3 and 4, the light sensitive layer 4 may be provided via an intermediate layer 5 formed on the electroconductive support 1. When the light sensitive layer 4 is formed into such a double layer structure, electrophotographic photoreceptors having the best electrophotographic characteristics are obtainable. However, in the present invention, a light sensitive layer 4 having fine powdery carrier generation material 7 dispersed in a layer 6 composed mainly of a carrier transport material, may be, directly or via an intermediate layer 5, provided on the electroconductive support 1, as shown in FIGS. 5 and 6.

In forming the light sensitive layer 4 into a double layer structure, the carrier generation layer 2 is, directly or via an intermediate layer such as an adhesive layer or a barrier layer, formed on the electroconductive support 1 or on the carrier transport layer 3 by one of the following methods: (1) a vacuum vapour deposition method, (2) a method of coating a solution prepared by dissolving the carrier generation material in a proper solvent, and (3) a method of coating a dispersion prepared by pulverizing the carrier generation material into fine particles in a dispersion medium by means of a ball mill or homogenizing mixer and mixing and dispersing it with a binder as the case requires.

The thickness of the carrier generation layer 2 thus formed is preferably from 0.01 to 5 microns, more preferably from 0.05 to 3 microns.

Further, the thickness of the carrier transport layer 3 may be varied as the case requires, whereas, in a usual case, it is preferably from 5 to 30 microns. The proportions of the consitutents in this carrier transport layer 3 are preferably such that the binder is in an amount of from 0.8 to 10 parts by weight relative to one part by weight of the carrier transport material containing the above mentioned carbazole derivative. However, in the case where a light sensitive layer 4 having fine powdery carrier generation material dispersed therein is to be formed, it is preferred to use the binder in an amount within a range of at most 5 parts by weight relative to one part by weight of the carrier generation material. Further, when the carrier generation layer 2 is formed into a dispersion type with the binder, it is likewise preferred to use the binder in an amount within a range of at most 5 parts by weight relative to one part by weight of the carrier generation material.

As the electroconductive support 1, there may be used a paper, a plastic film or a metal sheet, to which electroconductivity has been imparted by coating, vapour depositing or laminating an electroconductive compound such as an electroconductive polymer or indium oxide, or a thin metal film layer such as aluminum, palladium, or gold. As the intermediate layer 5, there may be used, in addition to polymers used for the above mentioned binders, organic polymers such as gelatin, casein, starch, vinyl acetate, polyvinyl alcohol, ethyl cellulose or carboxymethyl cellulose, or aluminum oxide.

The electrophotographic photoreceptors of the present invention have the above described construction, and as will be apparent from the following examples, they are superior in the electric charge characteristic, sensitivity characteristic, and image forming characteristic, and particularly, they undergo minimal fatigue degradations when used repeatedly and thus they are superior in their durability.

EXAMPLE 1

On an electroconductive support prepared by laminating an aluminum foil on a polyester film, selenium was vapour-deposited in a thickness of 0.5 μm to form a carrier generation layer. Then, 3 parts by weight of the illustrated compound (1) and 10 parts by weight of polycarbonate "Panlite L-1250" (manufactured by Teijin Chemicals, Ltd.) were dissolved in 90 parts by weight of 1,2-dichloroethane, and the solution thereby obtained was applied to form a carrier transport layer having a film thickness after drying of 11 μm, whereupon an electrophotographic photoreceptor of the present invention was prepared.

With respect to this electrophotographic photoreceptor, the electrophotographic characteristics were measured by a dynamic system by means of an electrostatic copying paper tester "SP-428 Model" (manufactured by Kawaguchi Electric Works Co., Ltd.). Namely, the surface of the light sensitive layer of the above photoreceptor was charged for 5 seconds with a voltage of 6.0 KV applied to the charging corona discharger, whereby the surface electric potential was designated as VA. Then, the light from a tungsten lamp was radiated so that the illumination at the surface of the photoreceptor was 35 lux and the exposure quantity E½(i.e. half-decay exposure) (lux·sec.) required to reduce the surface electric potential VA to a half-value and the surface electric potential (residual electric potential) VR after the exposure with an exposure quantity of 30 lux·sec., were respectively measured.

The same measurement was repeated 10 times. The results thereby obtained are shown in Table 1.

TABLE 1

|  | 1st time | 10th time |
|---|---|---|
| VA (V) | −915 | −920 |
| E½ (lux · sec.) | 8.2 | 8.5 |
| VR (V) | 0 | 0 |

EXAMPLE 2

On an electroconductive support prepared by laminating an aluminum foil on a polyester film, an intermediate layer having a thickness of 0.05 μm and composed of a vinyl chloride-vinyl acetate-maleic anhydride copolymer "S-Lec MF-10" (manufactured by Sekisui Chemical Co., Ltd.) was provided, and dibromoanthanthrone "Monolite Red 2Y" (CI No. 59300 manufactured by ICI Co.) was vapour-deposited thereon to form a carrier generation layer having a thickness of 0.5 μm. Then, a coating solution prepared by dissolving 6 parts by weight of the illustrated compound (3) and 10 parts by weight of polycarbonate "Jupilon S-1000" (manufactured by Mitsubishi Gas Chemical Co., Inc.) in 90 parts by weight of 1,2-dichloroethane, was applied to form a carrier transport layer having a film thickness after drying of 10 μm, whereupon an electrophotographic photoreceptor of the present invention was prepared.

With respect to this electrophotographic photoreceptor, the same measurements as in Example 1 were taken. The results thereby obtained are as shown in Table 2.

TABLE 2

|    | 1st time | 10th time |
|----|----------|-----------|
| VA | −845     | −855      |
| E½ | 2.9      | 3.0       |
| VR | 0        | 0         |

Further, to this photoreceptor, the light from a super high pressure mercury lamp "SHL-100 UV" (manufactured by Toshiba) was radiated from a distance of 5 cm for 30 seconds, and similar measurements were conducted, whereby VA=−860 V, E½=3.1 lux·sec., and VR=OV were obtained. It is seen that when compared with the results obtained prior to the radiation of the ultraviolet ray, there is no substantial change in the characteristics, and thus that the photoreceptor is quite stable against light.

COMPARATIVE EXAMPLE 1

A comparative photoreceptor was prepared in the same manner as in Example 2 except that a compound represented by the following formula was used as the carrier transport material:

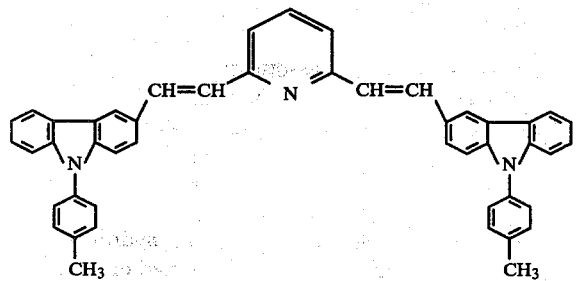

The measurements were conducted in a manner similar to Example 1. The results thereby obtained are as shown in Table 3.

TABLE 3

|              | 1st time | 10th time |
|--------------|----------|-----------|
| VA (V)       | −555     | −680      |
| E½ (lux·sec.)| 7.3      | 12.5      |
| VR (V)       | −22      | −70       |

EXAMPLE 3

One part by weight of Chloro Dian Blue represented by the following structural formula was dissolved in 140 parts by weight of a mixed solution prepared by mixing ethylene diamine, n-butylamine and tetrahydrofuran in a weight ratio of 1.2:1.0:2.2, and the solution thereby obtained was coated on the electroconductive support provided with an intermediate layer as used in Example 2 so that the amount of deposit after drying was 0.2 g/m², whereby a carrier generation layer was formed. Further, there was coated thereon a solution prepared by dissolving 3 parts by weight of the illustrated compound (B 5) and 10 parts by weight of a methacrylic resin "Acrypet" (manufactured by Mitsubishi Rayon Co., Ltd.) in 90 parts by weight of 1,2-dichloroethane so that the film thickness after drying was 11 μm, to form a carrier transport layer, whereupon a photoreceptor of the present invention (A) was prepared.

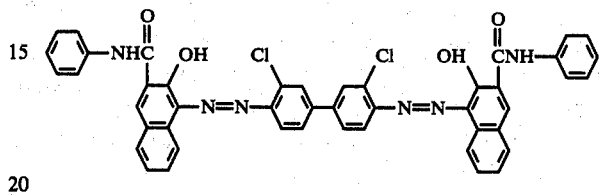

With respect to this photoreceptor, the sensitivity was measured in a manner similar to Example 1, whereby the half decay exposure E½ was found to be 2.7 lux·sec.

COMPARATIVE EXAMPLE 2

An attempt was made to prepare a comparative photoreceptor in accordance with the method of Example 3 except that a compound having the following structural formula was used as the carrier transport material.

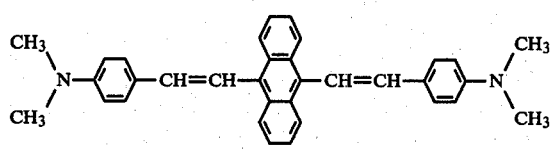

However, the above compound was almost insoluble in the solvent, and therefore, the mixed solution of the carrier generation layer was pulverized into a particle size of at most 1 μm by means of a ball mill and then dispersed. The dispersion thereby obtained was coated on the carrier generation layer, whereby a comparative photoreceptor was prepared.

The carrier transport layer of the comparative photoreceptor thus obtained was heterogeneous and poor in light transmission as well as in the electric charge acceptance and sensitivity, and thus it was not qualified for practical use as an electrophotographic photoreceptor. The results are shown in FIG. 7.

Figure 7:
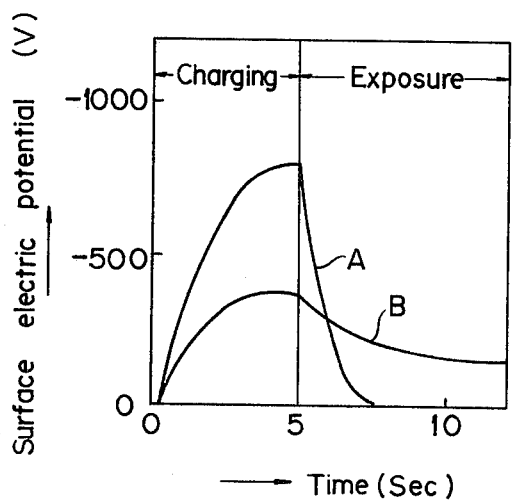
FIG. 7 shows the charging electric potential curve and the light decay curve of the photoreceptor of the invention and the comparative photoreceptor.

FIG. 7 shows the charging electric potential curve and light decay curve in the case where charging and exposure were applied to the photoreceptor (A) of the present invention of Example 3 and the photoreceptor of the Comparative Example 2. It will be seen that the photoreceptor of the present invention is substantially superior to the comparative photoreceptor in both the charging electric potential characteristic and the light decay characteristic.

EXAMPLE 4

On an electroconductive support prepared by laminating an aluminum foil on a polyester film, an intermediate layer having a thickness of 0.05 μm and composed of polyester "Vylon 200" (manufactured by Toyobo, Co., Ltd.) was provided, and there was coated thereon a solution prepared by dissolving 1 part by weight of 4-(p-dimethylaminophenyl)-2,6-diphenylthiapyrillium perchlorate in 130 parts by weight of dichloromethane, adding and dissolving thereto 10 parts by weight of polycarbonate "Panlite L-1250" (manufactured by Teijin Chemicals, Ltd.) and further adding and dissolving thereto 3 parts by weight of the illustrated compound (13) followed by adequate stirring, so that the film thickness after the drying was 13 μm, to form a light sensitive layer, whereupon a photoreceptor of the present invention was prepared.

With respect to this electrophotographic photoreceptor, the sensitivity was measured in the same manner as in Example 1, whereby the half exposure quantity $E_{\frac{1}{2}}$ was found to be 1.41 lux·sec. and the residual electric potential VR was found to be 0 volt. This photoreceptor was mounted on an electrophotographic copying machine "U-Bix 2000 R" (manufactured by Konishiroku Photo Industry Co., Ltd.) and an image was copied, whereupon a clear reproduction of the image was obtained which was almost identical with the original image and which was superior in contrast and gradation. This was subjected to continuous copying for 2000 times, whereby a reproduced image having the same quality as the initial reproduction was obtained.

EXAMPLE 5

On the electroconductive support provided with an intermediate layer, which was used in Example 2, N,N-dimethylperylene-3,4,9,10-tetracarboxylic acid diimide "Paliogen Maloon 3920" (i.e. C.I. No. 71130 manufactured by BASF) was vapour-deposited to form a carrier generation layer having a thickness of 0.5 μm. Then, 2.5 parts by weight of the illustrated compound (11) and 10 parts by weight of polyester "Polyester Adhesive 49000" (manufactured by Du Pont Co.) were dissolved in 90 parts by weight of 1,2-dichloroethane, and the solution thereby obtained was coated so that the film thickness after drying was 11 μm, to form a carrier transport layer, whereupon an electrophotographic photoreceptor of the present invention was prepared.

With respect to this photoreceptor, the sensitivity was measured in a manner similar to Example 1, whereby the half exposure quantity $E_{\frac{1}{2}}$ was found to be 6.2 lux·sec. and the residual electric potential VR was found to be −5 V.

EXAMPLES 6 TO 8

Electrophotographic photoreceptors of the present invention were prepared in a manner similar to Example 2 except that the illustrated compounds (13), (14) and (15) were used as the carrier transport material, and their sensitivity and residual electric potentials were measured in a manner similar to Example 1.

The results thereby obtained are as shown in Table 4.

TABLE 4

| Illustrated compounds | (13) | (14) | (15) |
|---|---|---|---|
| $E_{\frac{1}{2}}$ (lux · sec.) | 2.7 | 3.0 | 2.8 |
| VR (V) | 0 | 0 | 0 |

EXAMPLE 9

An electrophotographic photoreceptor of the present invention was prepared in a manner similar to Example 1 except that the illustrated compound (12) was used as the carrier transport material, and the measurements were conducted in a manner similar to Example 1. The results thereby obtained are as shown in Table 5.

TABLE 5

|  | 1st time | 10th time |
|---|---|---|
| VA (V) | −685 | −760 |
| $E_{\frac{1}{2}}$ (lux · sec.) | 10.8 | 12.4 |
| VR (V) | −10 | −45 |

From the results of the above Examples 1 to 9, it is seen that the photoreceptors using the carbazole derivatives according to the present invention, are superior to the comparative photoreceptors using the comparative compounds instead of the carbazole derivatives, in their residual electric potential characteristics and repeated characteristics.

We claim:

1. An electrophotographic photoreceptor comprising, a light sensitive layer on a conductive support, said light sensitive layer containing a carrier generation material and a carrier transport material comprising a carbazole derivative represented by formula I:

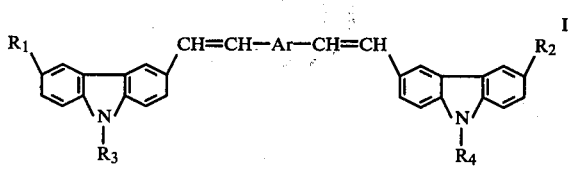

where each of $R_1$ and $R_2$ represents a hydrogen, a halogen, a hydroxy group, a substituted or unsubstituted alkyl group, an alkoxy group, an aryloxy group, a substituted amino group, or a substituted or unsubstituted aryl group; each of $R_3$ and $R_4$ represents a substituted or unsubstituted aryl group; and Ar represents a substituted or unsubstituted arylene group, or a divalent heterocyclic aromatic group, except pyridine.

2. The electrophotographic photoreceptor according to claim 1, wherein said light sensitive layer is composed of a double layer comprising a layer containing the carrier generation material and a layer containing said carbazole derivative as the carrier transport material.

3. The electrophotographic photoreceptor according to claim 1, wherein said carbazole derivative is selected from the group consisting of:

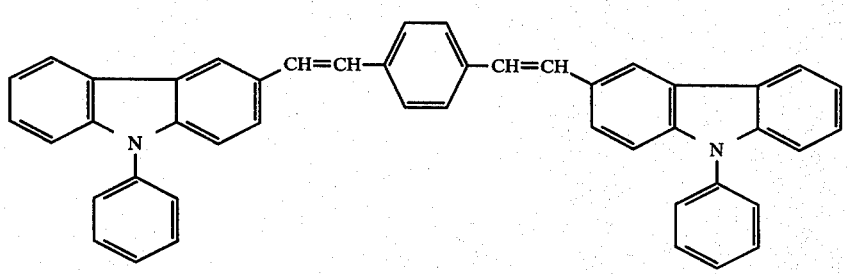
(1)
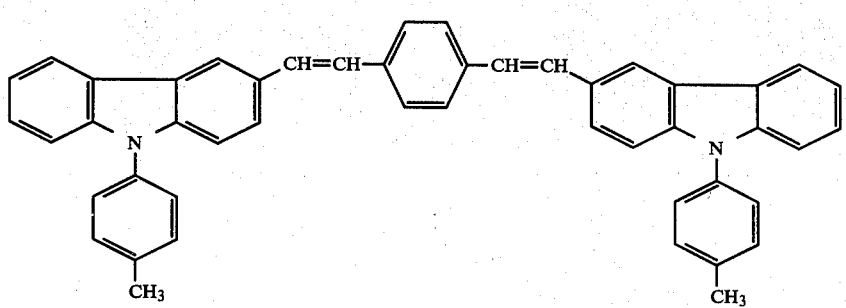
(2)
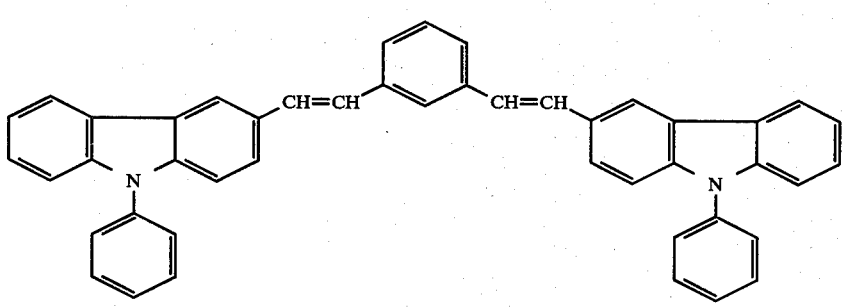
(3)
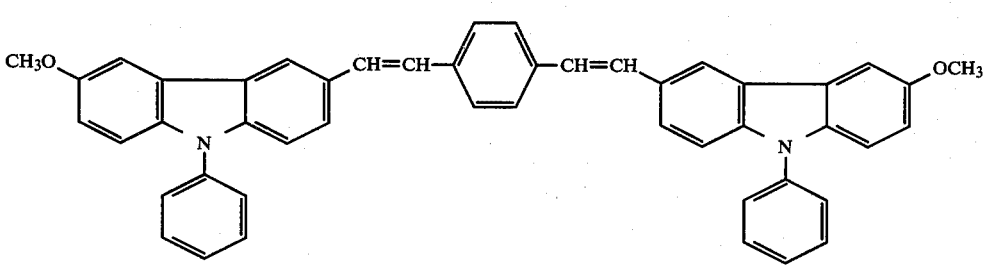
(4)
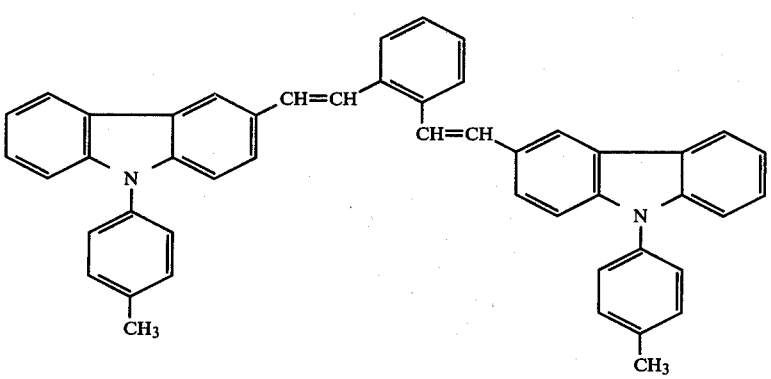
(5)

-continued
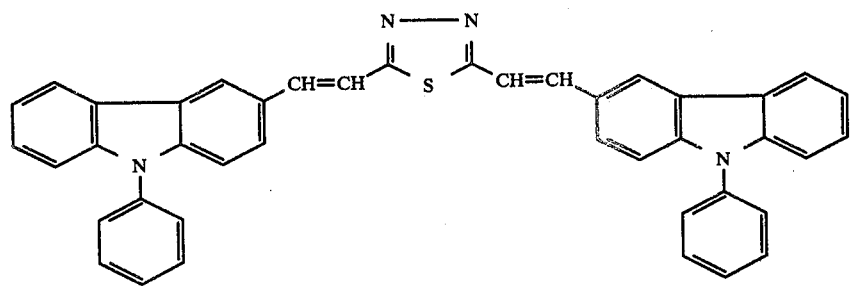 (6)
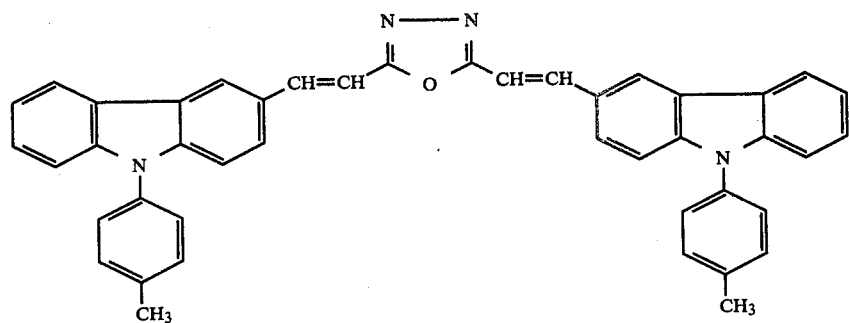 (7)
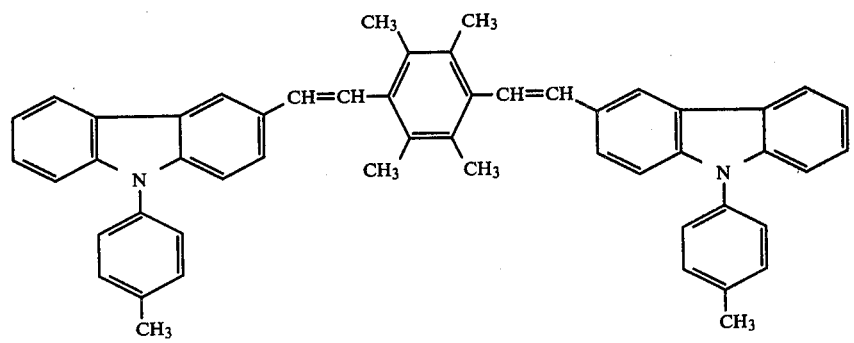 (8)
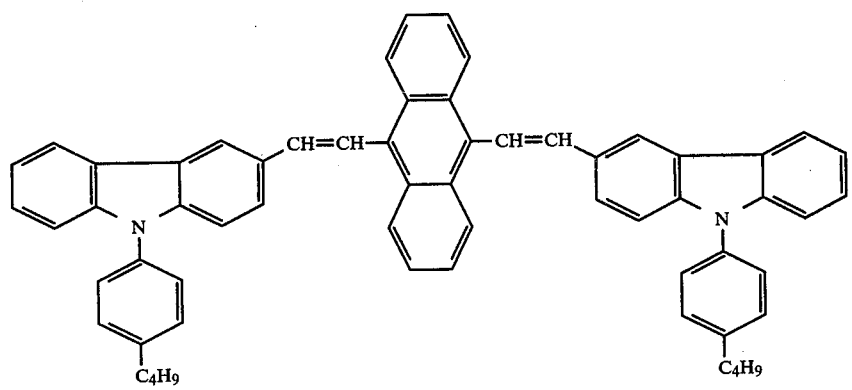 (9)
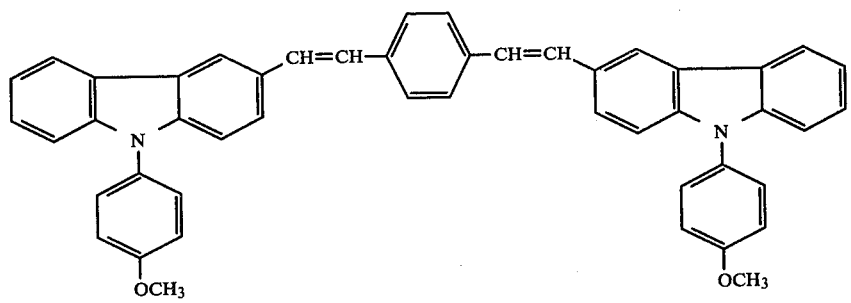 (10)

-continued

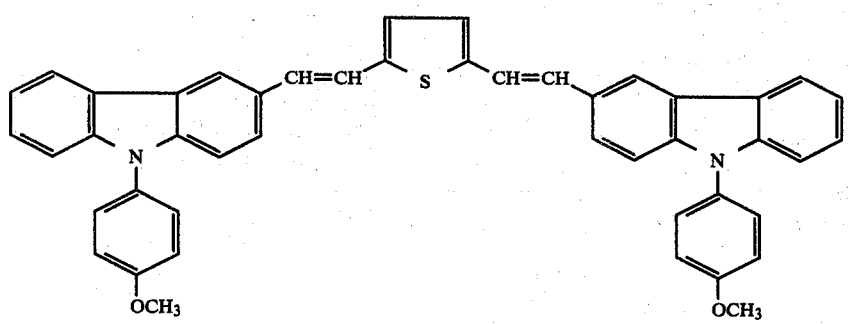
(11)

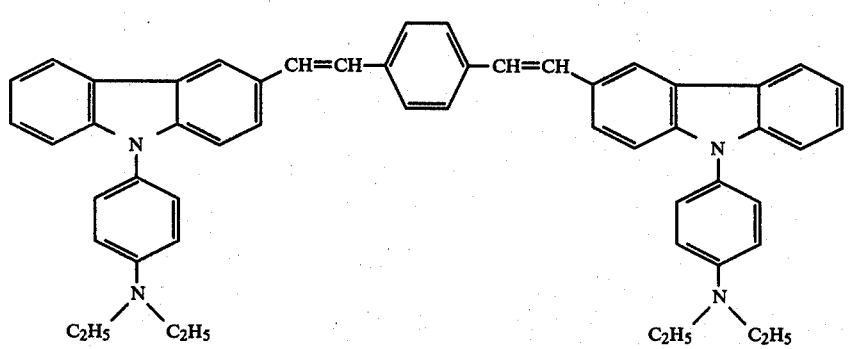
(12)

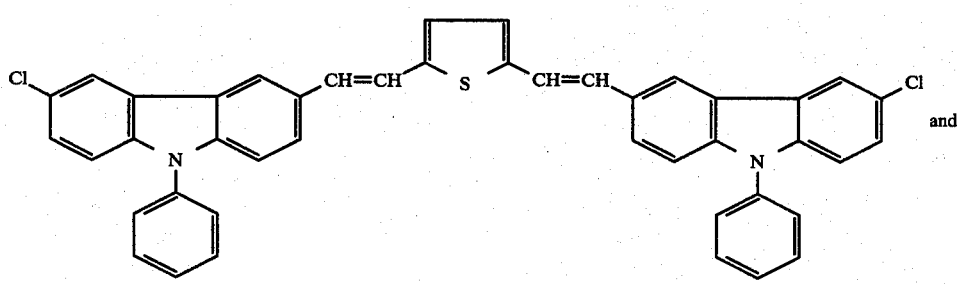
(13)

and

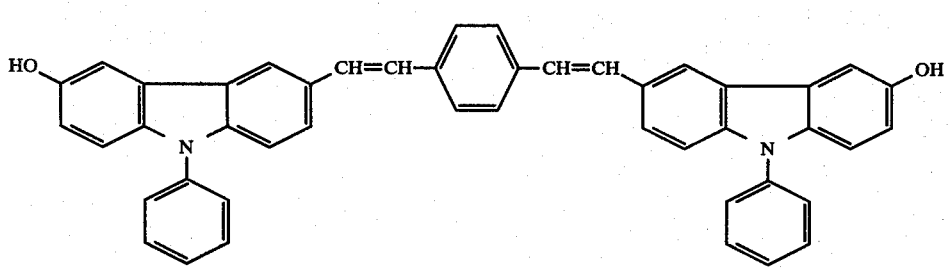
(14)

4. The electrophotographic photoreceptor according to claim 3, wherein one or more kinds of said carbazole derivative may be used, or may be used in combination with the carrier transport material.

5. The electrophotographic photoreceptor according to claim 3, wherein said carbazole derivative may be used in combination with a binder.

6. The electrophotographic photoreceptor according to claim 5, wherein said binder is selected from the group consisting of a polycarbonate, a polyester, a methacrylic resin, an acrylic resin, a polyvinyl chloride, a polyvinylidene chloride, a polystyrene, a polyvinyl acetate, a styrene-butadiene copolymer, a vinylidene chloride-acrylonitrile copolymer, a vinyl chloride-vinyl acetate copolymer, a vinyl chloride-vinyl acetate-anhydrous maleic acid copolymer, a silicone resin, a silicone-alkyd resin, a styrene-alkyd resin and a phenol formaldehyde resin.

7. The electrophotographic photoreceptor according to claim 1, wherein said carrier generation material is selected from the group consisting of inorganic photoconductors, perylene dyestuffs, indigoid dyestuffs, polycyclic quinones, bisbenzimidazole dyestuffs, quinachridone dyestuffs, azo dyestuffs, indanthrone dyestuffs, squarylium dyestuffs, phthalocyanine dyestuffs, charge-transfer complexes composed of electron donating substances and electron accepting substances, and co-crystalline complexes composed of pyrylium salts of thiapyrylium salts and polycarbonate.

8. The electrophotographic photoreceptor according to claim 2, wherein the layer containing the carrier generation material has a thickness of from 0.01 to 5 microns.

9. The electrophotographic photoreceptor according to claim 2, wherein the layer containing the carbazole derivative has a thickness of from 5 to 30 microns.

10. The electrophotographic photoreceptor according to claim 3, wherein said carrier generation material is selected from the group consisting of inorganic photoconductors, perylene dyestuffs, indigoid dyestuffs, polycyclic quinones, bisbenzimidazole dyestuffs, quinachridone dyestuffs, azo dyestuffs, indanthrone dyestuffs, squarylium dyestuffs, phthalocyanine dyestuffs, charge-transfer complexes composed of electron donating substances and electron accepting substances, and co-crystalline complexes composed of pyrylium salts or thiapyrylium salts and polycarbonate.

11. The electrophotographic photoreceptor according to claim 1, wherein said divalent heterocyclic aromatic group contains a heteroatom selected from oxygen and sulfur.

* * * * *